United States Patent
Crowley

(10) Patent No.: US 8,480,629 B2
(45) Date of Patent: Jul. 9, 2013

(54) UNIVERSAL UTILITY BOARD FOR USE WITH MEDICAL DEVICES AND METHODS OF USE

(75) Inventor: Peter Crowley, Norfolk, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1738 days.

(21) Appl. No.: 11/046,291

(22) Filed: Jan. 28, 2005

(65) Prior Publication Data

US 2006/0173438 A1    Aug. 3, 2006

(51) Int. Cl.
*A61M 5/32*    (2006.01)
*A61M 31/00*    (2006.01)

(52) U.S. Cl.
USPC .......................................... 604/174; 604/500

(58) Field of Classification Search
USPC ................ 604/174, 177–180, 275, 277, 278, 604/523, 104–106, 167.06, 164.01, 604/170.01–170.03, 268, 536, 103.08, 500
See application file for complete search history.

(56) References Cited

U.S. PATENT DOCUMENTS

| | | |
|---|---|---|
| 1,204,053 A | 11/1916 | Moore |
| 2,623,520 A | 12/1952 | Bamford, Jr. et al. |
| 3,015,869 A | 1/1962 | Rapata |
| 3,251,069 A | 5/1966 | Clark |
| 3,472,230 A | 10/1969 | Fogarty |
| 3,536,281 A | 10/1970 | Meehan et al. |
| 3,592,186 A | 7/1971 | Oster |
| 3,683,904 A | 8/1972 | Forster |
| 3,747,166 A * | 7/1973 | Eross ............................... 248/75 |
| 3,889,657 A | 6/1975 | Baumgarten |
| 3,952,747 A | 4/1976 | Kimmell, Jr. |
| 3,996,938 A | 12/1976 | Clark, III |
| 4,020,829 A | 5/1977 | Willson et al. |
| 4,029,103 A | 6/1977 | McConnell |
| 4,046,150 A | 9/1977 | Schwartz et al. |
| 4,345,606 A | 8/1982 | Littleford |
| 4,411,654 A | 10/1983 | Boarini et al. |
| 4,412,832 A | 11/1983 | Kling et al. |
| 4,417,710 A | 11/1983 | Adair |
| 4,419,094 A | 12/1983 | Patel |
| 4,425,908 A | 1/1984 | Simon |
| 4,447,227 A | 5/1984 | Kotsanis |

(Continued)

FOREIGN PATENT DOCUMENTS

| | | |
|---|---|---|
| DE | 28 21 048 C2 | 11/1979 |
| DE | 34 17 738 A1 | 11/1985 |

(Continued)

OTHER PUBLICATIONS

Arndorfer Inc. Information Sheet, dated on or before Mar. 6, 2000, 7 sheets.

(Continued)

*Primary Examiner* — Kevin C Sirmons
*Assistant Examiner* — Andrew Gilbert
(74) *Attorney, Agent, or Firm* — Bookoff McAndrews, PLLC

(57) ABSTRACT

A utility fixture secured to a proximal portion of an elongate medical device and methods of use. The utility fixture may have one or more receptacles for receiving and retaining additional medical instruments. The utility fixture may provide the operator a means to free a hand during a medical procedure. Therefore, the operator may operate a plurality of medical instruments simultaneously and/or sequentially during a medical procedure without assistance.

34 Claims, 6 Drawing Sheets

U.S. PATENT DOCUMENTS

| | | |
|---|---|---|
| 4,474,174 A | 10/1984 | Petruzzi |
| RE31,855 E | 3/1985 | Osborne |
| 4,580,568 A | 4/1986 | Gianturco |
| 4,590,938 A | 5/1986 | Segura et al. |
| 4,612,053 A | 9/1986 | Brown et al. |
| 4,619,246 A | 10/1986 | Molgaard-Nielsen et al. |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa, Jr. |
| 4,696,668 A | 9/1987 | Wilcox |
| 4,700,694 A | 10/1987 | Shishido |
| 4,705,517 A | 11/1987 | DiPisa, Jr. |
| 4,706,671 A | 11/1987 | Weinrib |
| 4,715,360 A | 12/1987 | Akui et al. |
| 4,723,549 A | 2/1988 | Wholey et al. |
| 4,728,319 A | 3/1988 | Masch |
| 4,733,665 A | 3/1988 | Palmaz |
| 4,748,982 A | 6/1988 | Horzewski et al. |
| 4,762,129 A | 8/1988 | Bonzel |
| 4,771,777 A | 9/1988 | Horzewski et al. |
| 4,781,677 A | 11/1988 | Wilcox |
| 4,790,812 A | 12/1988 | Hawkins, Jr. et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,835,824 A | 6/1989 | Durham et al. |
| 4,842,579 A | 6/1989 | Shiber |
| 4,844,092 A | 7/1989 | Rydell et al. |
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg |
| 4,886,061 A | 12/1989 | Fischell et al. |
| 4,898,575 A | 2/1990 | Fischell et al. |
| 4,900,184 A | 2/1990 | Cleveland |
| 4,905,667 A | 3/1990 | Foerster et al. |
| 4,907,336 A | 3/1990 | Gianturco |
| 4,917,103 A | 4/1990 | Gambale et al. |
| 4,921,478 A | 5/1990 | Solano et al. |
| 4,921,484 A | 5/1990 | Hillstead |
| 4,926,858 A | 5/1990 | Gifford, III et al. |
| 4,927,418 A | 5/1990 | Dake et al. |
| 4,928,669 A | 5/1990 | Sullivan |
| 4,928,693 A | 5/1990 | Goodin et al. |
| 4,932,413 A | 6/1990 | Shockey et al. |
| 4,946,443 A | 8/1990 | Hauser et al. |
| 4,950,277 A | 8/1990 | Farr |
| 4,955,895 A | 9/1990 | Sugiyama et al. |
| 4,957,482 A | 9/1990 | Shiber |
| 4,969,891 A | 11/1990 | Gewertz |
| 4,973,329 A | 11/1990 | Park et al. |
| 4,979,951 A | 12/1990 | Simpson |
| 4,983,168 A | 1/1991 | Moorehead |
| 4,986,807 A | 1/1991 | Farr |
| 4,988,356 A | 1/1991 | Crittenden et al. |
| 4,995,872 A | 2/1991 | Ferrara |
| 4,997,421 A | 3/1991 | Palsrok et al. |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,031,636 A | 7/1991 | Gambale et al. |
| 5,040,548 A | 8/1991 | Yock |
| 5,041,126 A | 8/1991 | Gianturco |
| 5,047,045 A | 9/1991 | Arney et al. |
| 5,053,008 A | 10/1991 | Bajaj |
| 5,053,044 A | 10/1991 | Mueller et al. |
| 5,055,109 A | 10/1991 | Gould et al. |
| 5,061,273 A | 10/1991 | Yock |
| 5,064,414 A | 11/1991 | Revane |
| 5,071,407 A | 12/1991 | Termin et al. |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,419 A | 4/1992 | Reger et al. |
| 5,114,403 A | 5/1992 | Clarke et al. |
| 5,125,915 A | 6/1992 | Berry et al. |
| 5,133,733 A | 7/1992 | Rasmussen et al. |
| 5,135,531 A | 8/1992 | Shiber |
| 5,135,535 A | 8/1992 | Kramer |
| 5,139,032 A | 8/1992 | Jahrmarkt et al. |
| 5,147,377 A | 9/1992 | Sahota |
| 5,152,771 A | 10/1992 | Sabbaghian et al. |
| 5,152,777 A | 10/1992 | Goldberg et al. |
| 5,156,594 A | 10/1992 | Keith |
| 5,158,545 A | 10/1992 | Trudell et al. |
| 5,160,342 A | 11/1992 | Reger et al. |
| 5,167,634 A | 12/1992 | Corrigan, Jr. et al. |
| 5,171,233 A | 12/1992 | Amplatz et al. |
| 5,180,367 A | 1/1993 | Kontos et al. |
| 5,190,546 A | 3/1993 | Jervis |
| 5,191,888 A | 3/1993 | Palmer et al. |
| 5,195,955 A | 3/1993 | Don Michael |
| 5,195,978 A | 3/1993 | Schiffer |
| 5,205,822 A | 4/1993 | Johnson et al. |
| 5,224,953 A | 7/1993 | Morgentaler |
| 5,232,445 A | 8/1993 | Bonzel |
| 5,248,306 A | 9/1993 | Clark et al. |
| 5,250,033 A | 10/1993 | Evans et al. |
| 5,263,932 A | 11/1993 | Jang |
| 5,267,958 A | 12/1993 | Buchbinder et al. |
| 5,269,759 A | 12/1993 | Hernandez et al. |
| 5,279,562 A | 1/1994 | Sirhan et al. |
| 5,281,203 A | 1/1994 | Ressemann |
| 5,282,479 A | 2/1994 | Havran |
| 5,290,232 A | 3/1994 | Johnson et al. |
| 5,290,241 A | 3/1994 | Kraus et al. |
| 5,300,085 A | 4/1994 | Yock |
| 5,306,247 A | 4/1994 | Pfenninger |
| 5,306,286 A | 4/1994 | Stack et al. |
| 5,308,318 A | 5/1994 | Plassche, Jr. |
| 5,312,338 A | 5/1994 | Nelson et al. |
| 5,314,444 A | 5/1994 | Gianturco |
| 5,314,472 A | 5/1994 | Fontaine |
| 5,318,576 A | 6/1994 | Plassche, Jr. et al. |
| 5,320,602 A | 6/1994 | Karpiel |
| 5,324,259 A | 6/1994 | Taylor et al. |
| 5,324,269 A | 6/1994 | Miraki |
| 5,328,472 A | 7/1994 | Steinke et al. |
| 5,329,942 A | 7/1994 | Gunther et al. |
| 5,330,484 A | 7/1994 | Gunther |
| 5,330,500 A | 7/1994 | Song |
| 5,334,143 A | 8/1994 | Carroll |
| 5,334,147 A | 8/1994 | Johnson |
| 5,334,187 A | 8/1994 | Fischell et al. |
| 5,336,179 A * | 8/1994 | Ryan ............................... 604/80 |
| 5,336,184 A | 8/1994 | Teirstein |
| 5,342,297 A | 8/1994 | Jang |
| 5,350,395 A | 9/1994 | Yock |
| 5,350,398 A | 9/1994 | Pavcnik et al. |
| 5,354,310 A | 10/1994 | Garnic et al. |
| 5,356,423 A | 10/1994 | Tihon et al. |
| 5,357,978 A | 10/1994 | Turk |
| 5,364,355 A | 11/1994 | Alden et al. |
| 5,364,376 A | 11/1994 | Horzewski et al. |
| 5,366,444 A | 11/1994 | Martin |
| 5,366,464 A | 11/1994 | Belknap |
| 5,366,473 A | 11/1994 | Winston et al. |
| 5,368,567 A | 11/1994 | Lee |
| 5,370,623 A | 12/1994 | Kreamer |
| 5,370,657 A | 12/1994 | Irie |
| 5,370,683 A | 12/1994 | Fontaine |
| 5,372,592 A | 12/1994 | Gambale |
| 5,376,100 A | 12/1994 | Lefebvre |
| 5,380,283 A | 1/1995 | Johnson |
| 5,383,887 A | 1/1995 | Nadal |

| Patent No. | | Date | Inventor(s) | Patent No. | | Date | Inventor(s) |
|---|---|---|---|---|---|---|---|
| 5,383,892 | A | 1/1995 | Cardon et al. | 5,669,933 | A | 9/1997 | Simon et al. |
| 5,383,926 | A | 1/1995 | Lock et al. | 5,685,853 | A | 11/1997 | Bonnet |
| 5,387,226 | A | 2/1995 | Miraki | 5,693,015 | A | 12/1997 | Walker et al. |
| 5,387,235 | A | 2/1995 | Chuter | 5,695,519 | A | 12/1997 | Summers et al. |
| 5,388,579 | A | 2/1995 | Dowd et al. | 5,695,729 | A | 12/1997 | Chow et al. |
| 5,389,087 | A | 2/1995 | Miraki | 5,706,827 | A | 1/1998 | Ehr et al. |
| 5,392,778 | A | 2/1995 | Horzewski | 5,709,704 | A | 1/1998 | Nott et al. |
| 5,395,335 | A | 3/1995 | Jang | 5,718,680 | A | 2/1998 | Kraus et al. |
| 5,395,349 | A | 3/1995 | Quiachon et al. | 5,720,764 | A | 2/1998 | Naderlinger |
| 5,397,302 | A | 3/1995 | Weaver et al. | 5,725,504 | A | 3/1998 | Collins |
| 5,397,345 | A | 3/1995 | Lazerus | 5,728,047 | A | 3/1998 | Edoga |
| 5,405,110 | A * | 4/1995 | Mistretta ............... 604/174 | 5,728,066 | A | 3/1998 | Daneshvar |
| 5,405,377 | A | 4/1995 | Cragg | 5,730,150 | A | 3/1998 | Peppel et al. |
| 5,409,454 | A | 4/1995 | Fischell et al. | 5,746,758 | A | 5/1998 | Nordgren et al. |
| 5,409,459 | A | 4/1995 | Gambale | 5,749,370 | A | 5/1998 | Brooks et al. |
| 5,413,559 | A | 5/1995 | Sirhan et al. | 5,749,848 | A | 5/1998 | Jang et al. |
| 5,415,630 | A | 5/1995 | Gory et al. | 5,769,816 | A | 6/1998 | Barbut et al. |
| 5,415,639 | A | 5/1995 | VandenEinde et al. | 5,776,080 | A | 7/1998 | Thome et al. |
| 5,419,774 | A | 5/1995 | Willard et al. | 5,779,716 | A | 7/1998 | Cano et al. |
| 5,421,832 | A | 6/1995 | Lefebvre | 5,782,971 | A | 7/1998 | Constantz et al. |
| 5,423,742 | A | 6/1995 | Theron | 5,788,681 | A | 8/1998 | Weaver et al. |
| 5,423,885 | A | 6/1995 | Williams | 5,792,157 | A | 8/1998 | Mische et al. |
| 5,425,765 | A | 6/1995 | Tiefenbrun et al. | 5,792,300 | A | 8/1998 | Inderbitzen et al. |
| 5,438,993 | A | 8/1995 | Lynch et al. | 5,795,322 | A | 8/1998 | Boudewijn |
| 5,443,498 | A | 8/1995 | Fontaine | 5,795,335 | A * | 8/1998 | Zinreich ............... 604/174 |
| 5,448,993 | A | 9/1995 | Lynch et al. | 5,797,952 | A | 8/1998 | Klein |
| 5,449,349 | A * | 9/1995 | Sallee et al. ............ 604/180 | 5,800,414 | A | 9/1998 | Cazal |
| 5,449,363 | A | 9/1995 | Brust et al. | 5,800,457 | A | 9/1998 | Gelbfish |
| 5,449,372 | A | 9/1995 | Schmaltz et al. | 5,800,525 | A | 9/1998 | Bachinski et al. |
| 5,451,233 | A | 9/1995 | Yock | 5,807,398 | A | 9/1998 | Shaknovich |
| 5,454,790 | A | 10/1995 | Dubrul | 5,810,874 | A | 9/1998 | Lefebvre |
| 5,456,667 | A | 10/1995 | Ham et al. | 5,814,064 | A | 9/1998 | Daniel et al. |
| 5,458,584 | A | 10/1995 | Ginn et al. | 5,817,102 | A | 10/1998 | Johnson et al. |
| 5,458,605 | A | 10/1995 | Klemm | 5,820,632 | A | 10/1998 | Constantz et al. |
| 5,462,529 | A | 10/1995 | Simpson et al. | 5,827,202 | A | 10/1998 | Miraki et al. |
| 5,462,530 | A | 10/1995 | Jang | 5,827,230 | A * | 10/1998 | Bierman ............... 604/174 |
| 5,464,023 | A | 11/1995 | Viera | 5,827,324 | A | 10/1998 | Cassell et al. |
| 5,476,104 | A | 12/1995 | Sheahon | 5,830,157 | A | 11/1998 | Foote |
| 5,480,389 | A | 1/1996 | McWha et al. | 5,830,183 | A | 11/1998 | Krieger |
| 5,484,418 | A | 1/1996 | Quiachon et al. | 5,833,644 | A | 11/1998 | Zadno-Azizi et al. |
| 5,487,729 | A | 1/1996 | Avellanet et al. | 5,833,650 | A | 11/1998 | Imran |
| 5,489,271 | A | 2/1996 | Andersen | 5,833,706 | A | 11/1998 | St. Germain et al. |
| 5,490,837 | A | 2/1996 | Blaeser et al. | 5,836,306 | A | 11/1998 | Duane et al. |
| 5,496,346 | A | 3/1996 | Horzewski et al. | 5,843,028 | A | 12/1998 | Weaver et al. |
| 5,501,227 | A | 3/1996 | Yock | 5,846,260 | A | 12/1998 | Maahs |
| 5,507,767 | A | 4/1996 | Maeda et al. | 5,848,964 | A | 12/1998 | Samuels |
| 5,512,044 | A | 4/1996 | Duer | 5,849,016 | A | 12/1998 | Suhr |
| 5,520,656 | A | 5/1996 | Byrd | 5,851,189 | A | 12/1998 | Forber |
| 5,527,354 | A | 6/1996 | Fontaine et al. | 5,876,367 | A | 3/1999 | Kaganov et al. |
| 5,531,700 | A | 7/1996 | Moore et al. | 5,893,867 | A | 4/1999 | Bagaoisan et al. |
| 5,536,242 | A | 7/1996 | Willard et al. | 5,895,399 | A | 4/1999 | Barbut et al. |
| 5,536,248 | A | 7/1996 | Weaver et al. | 5,897,584 | A | 4/1999 | Herman |
| 5,540,236 | A | 7/1996 | Ginn | 5,902,263 | A | 5/1999 | Patterson et al. |
| 5,540,707 | A | 7/1996 | Ressemann et al. | 5,906,618 | A | 5/1999 | Larson, III |
| 5,542,938 | A | 8/1996 | Avellanet et al. | 5,908,435 | A | 6/1999 | Samuels |
| 5,545,254 | A | 8/1996 | Chow et al. | 5,910,154 | A | 6/1999 | Tsugita et al. |
| 5,549,626 | A | 8/1996 | Miller et al. | 5,911,734 | A | 6/1999 | Tsugita et al. |
| 5,551,443 | A | 9/1996 | Sepetka et al. | 5,916,193 | A | 6/1999 | Stevens et al. |
| 5,555,893 | A | 9/1996 | Hackett et al. | 5,921,971 | A | 7/1999 | Agro et al. |
| 5,558,101 | A | 9/1996 | Brooks et al. | 5,925,016 | A | 7/1999 | Chornenky et al. |
| 5,562,724 | A | 10/1996 | Vorwerk et al. | 5,925,060 | A | 7/1999 | Forber |
| 5,569,274 | A | 10/1996 | Rapacki et al. | 5,925,062 | A | 7/1999 | Purdy |
| 5,569,275 | A | 10/1996 | Kotula et al. | 5,925,063 | A | 7/1999 | Khosravi |
| D375,890 | S * | 11/1996 | Takai ............... D8/380 | 5,928,203 | A | 7/1999 | Davey et al. |
| 5,570,701 | A | 11/1996 | Ellis et al. | 5,928,218 | A | 7/1999 | Gelbfish |
| 5,579,779 | A | 12/1996 | Humphrey | 5,934,284 | A | 8/1999 | Plaia et al. |
| 5,588,442 | A | 12/1996 | Scovil et al. | 5,935,114 | A | 8/1999 | Jang et al. |
| 5,599,299 | A | 2/1997 | Weaver et al. | 5,935,139 | A | 8/1999 | Bates |
| 5,599,300 | A | 2/1997 | Weaver et al. | 5,938,645 | A | 8/1999 | Gordon |
| 5,605,713 | A | 2/1997 | Boltong | 5,941,869 | A | 8/1999 | Patterson et al. |
| 5,606,980 | A | 3/1997 | Calhoun et al. | 5,941,896 | A | 8/1999 | Kerr |
| 5,613,949 | A | 3/1997 | Miraki | 5,944,701 | A | 8/1999 | Dubrul |
| 5,623,943 | A | 4/1997 | Hackett et al. | 5,947,995 | A | 9/1999 | Samuels |
| 5,626,600 | A | 5/1997 | Horzewski et al. | 5,951,585 | A | 9/1999 | Cathcart et al. |
| 5,630,427 | A | 5/1997 | Hastings | 5,954,707 | A | 9/1999 | Kanesaka et al. |
| 5,634,897 | A | 6/1997 | Dance et al. | 5,954,745 | A | 9/1999 | Gertler et al. |
| 5,652,016 | A | 7/1997 | Imura et al. | 5,976,172 | A | 11/1999 | Homsma et al. |
| 5,658,296 | A | 8/1997 | Bates et al. | 5,978,699 | A | 11/1999 | Fehse et al. |
| 5,662,671 | A | 9/1997 | Barbut et al. | 5,980,555 | A | 11/1999 | Barbut et al. |

| | | |
|---|---|---|
| 5,989,210 A | 11/1999 | Morris et al. |
| 5,989,271 A | 11/1999 | Bonnette et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,005,162 A | 12/1999 | Constantz |
| 6,007,522 A | 12/1999 | Agro et al. |
| 6,007,557 A | 12/1999 | Ambrisco et al. |
| 6,010,522 A | 1/2000 | Barbut et al. |
| 6,013,038 A | 1/2000 | Pflueger |
| 6,013,085 A | 1/2000 | Howard |
| 6,027,520 A | 2/2000 | Tsugita et al. |
| 6,027,742 A | 2/2000 | Lee et al. |
| 6,033,414 A | 3/2000 | Tockman et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,074,368 A | 6/2000 | Wright |
| 6,086,605 A | 7/2000 | Barbut et al. |
| 6,096,009 A | 8/2000 | Windheuser et al. |
| 6,117,154 A | 9/2000 | Barbut et al. |
| 6,117,456 A | 9/2000 | Lee et al. |
| 6,129,739 A | 10/2000 | Khosravi |
| 6,132,463 A | 10/2000 | Lee et al. |
| 6,136,016 A | 10/2000 | Barbut et al. |
| 6,139,578 A | 10/2000 | Lee et al. |
| 6,142,987 A | 11/2000 | Tsugita |
| 6,152,910 A | 11/2000 | Agro et al. |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,190,333 B1 | 2/2001 | Valencia |
| 6,200,262 B1 | 3/2001 | Ouchi |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,100 B1 | 8/2001 | Raulerson et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,312,404 B1 | 11/2001 | Agro et al. |
| 6,319,268 B1 | 11/2001 | Ambrisco et al. |
| 6,344,049 B1 | 2/2002 | Levinson et al. |
| 6,346,093 B1 | 2/2002 | Allman et al. |
| 6,371,940 B1 | 4/2002 | Valencia et al. |
| 6,458,104 B2 * | 10/2002 | Gautsche ............... 604/179 |
| 6,471,172 B1 | 10/2002 | Lemke et al. |
| 6,520,951 B1 | 2/2003 | Carrillo, Jr. et al. |
| 6,551,273 B1 | 4/2003 | Olson et al. |
| 6,582,401 B1 | 6/2003 | Windheuser et al. |
| 6,606,515 B1 | 8/2003 | Windheuser et al. |
| 6,656,199 B1 | 12/2003 | Lafontaine |
| 6,663,597 B1 | 12/2003 | Windheuser et al. |
| 6,746,442 B2 | 6/2004 | Agro et al. |
| 6,746,466 B2 | 6/2004 | Eidenschink et al. |
| 6,827,722 B1 | 12/2004 | Schoenefeld |
| D508,842 S * | 8/2005 | Paolini ............... D8/395 |
| 7,918,828 B2 * | 4/2011 | Lundgaard et al. ........ 604/174 |
| 8,317,149 B2 * | 11/2012 | Greenburg et al. ........ 248/316.7 |
| 2002/0087100 A1 | 7/2002 | Onuki et al. |
| 2002/0177869 A1 | 11/2002 | Eidenschink et al. |
| 2003/0014016 A1 * | 1/2003 | Purdy ............... 604/174 |
| 2004/0006329 A1 | 1/2004 | Scheu |
| 2004/0106852 A1 | 6/2004 | Windheuser et al. |
| 2004/0162465 A1 | 8/2004 | Carrillo |
| 2004/0199197 A1 | 10/2004 | Eidenschink et al. |

FOREIGN PATENT DOCUMENTS

| | | |
|---|---|---|
| DE | 40 30 998 A1 | 4/1991 |
| DE | 41 15 007 A1 | 11/1992 |
| DE | 198 23 064 A1 | 11/1999 |
| DE | 199 48 409 C1 | 4/2001 |
| EP | 0 200 688 A1 | 11/1986 |
| EP | 0 293 605 A1 | 12/1988 |
| EP | 0 328 760 A2 | 8/1989 |
| EP | 0 335 581 A2 | 10/1989 |
| EP | 0 388 112 A2 | 9/1990 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 792 657 A2 | 9/1997 |
| EP | 0 801 955 B1 | 10/1997 |
| EP | 0 852 132 A1 | 7/1998 |
| EP | 0 934 729 A1 | 8/1999 |
| FR | 2 580 504 A1 | 10/1986 |
| FR | 2 633 178 A1 | 12/1989 |
| FR | 2 643 250 A1 | 8/1990 |
| FR | 2 666 980 A1 | 3/1992 |
| FR | 2 768 326 A1 | 3/1999 |
| GB | 2 020 557 B | 11/1979 |
| JP | 8-187294 A | 7/1996 |
| JP | 9-10316 A | 1/1997 |
| JP | 9-239039 A | 9/1997 |
| JP | 111332992 | 7/1999 |
| SU | 764684 | 9/1980 |
| WO | WO 88/09683 A1 | 12/1988 |
| WO | WO 92/03097 A1 | 3/1992 |
| WO | WO 92/03963 A1 | 3/1992 |
| WO | WO 94/10915 A1 | 5/1994 |
| WO | WO 94/14389 A1 | 7/1994 |
| WO | WO 94/24946 A1 | 11/1994 |
| WO | WO 96/01591 A1 | 1/1996 |
| WO | WO 96/04875 A1 | 2/1996 |
| WO | WO 96/10375 A1 | 4/1996 |
| WO | WO 96/19941 A1 | 7/1996 |
| WO | WO 96/23441 A1 | 8/1996 |
| WO | WO 96/33677 A1 | 10/1996 |
| WO | WO 96/33764 A1 | 10/1996 |
| WO | WO 97/17100 A1 | 5/1997 |
| WO | WO 97/27808 A1 | 8/1997 |
| WO | WO 97/42879 A1 | 11/1997 |
| WO | WO 98/02084 A1 | 1/1998 |
| WO | WO 98/02112 A1 | 1/1998 |
| WO | WO 98/10820 A1 | 3/1998 |
| WO | WO 98/10821 A1 | 3/1998 |
| WO | WO 98/23322 A1 | 6/1998 |
| WO | WO 98/33443 A1 | 8/1998 |
| WO | WO 98/34673 A1 | 8/1998 |
| WO | WO 98/36786 A1 | 8/1998 |
| WO | WO 98/38920 A1 | 9/1998 |

| | | |
|---|---|---|
| WO | WO 98/38929 A1 | 9/1998 |
| WO | WO 98/39046 A1 | 9/1998 |
| WO | WO 98/39053 A1 | 9/1998 |
| WO | WO 98/46297 A1 | 10/1998 |
| WO | WO 98/47447 A1 | 10/1998 |
| WO | WO 98/49952 A1 | 11/1998 |
| WO | WO 98/50103 A1 | 11/1998 |
| WO | WO 98/51237 A1 | 11/1998 |
| WO | WO 98/55175 A1 | 12/1998 |
| WO | WO 99/09895 A1 | 3/1999 |
| WO | WO 99/22673 A1 | 5/1999 |
| WO | WO 99/23976 A1 | 5/1999 |
| WO | WO 99/25252 A1 | 5/1999 |
| WO | WO 99/30766 A1 | 6/1999 |
| WO | WO 99/38557 A1 | 8/1999 |
| WO | WO 99/40964 A1 | 8/1999 |
| WO | WO 99/42059 A2 | 8/1999 |
| WO | WO 99/44510 A1 | 9/1999 |
| WO | WO 99/44539 A2 | 9/1999 |
| WO | WO 99/44542 A2 | 9/1999 |
| WO | WO 99/45997 A1 | 9/1999 |
| WO | WO 99/47202 A1 | 9/1999 |
| WO | WO 99/55236 A1 | 11/1999 |
| WO | WO 99/55409 A1 | 11/1999 |
| WO | WO 99/58068 A2 | 11/1999 |
| WO | WO 99/59664 A1 | 11/1999 |
| WO | WO 00/07655 A1 | 2/2000 |
| WO | WO 00/09054 A1 | 2/2000 |
| WO | WO 00/13613 A1 | 3/2000 |
| WO | WO 00/16705 A1 | 3/2000 |
| WO | WO 00/49970 A1 | 8/2000 |
| WO | WO 00/69499 A1 | 11/2000 |
| WO | WO 00/69500 A1 | 11/2000 |
| WO | WO 01/43809 A1 | 6/2001 |

OTHER PUBLICATIONS

"Atherosclerotic Disease of the Aortic Arch as a Risk Factor of Recurrent Ischemic Stroke," *The New England Journal of Medicine*, May 9, 1996, pp. 1216-1221.

"Endovascular Grafts, Stents Drive Interventional Radiology Growth," *Cardiovascular Device Update*, Mar. 1996 vol. 2, No. 3, pp. 1-12.

Cragg, Andrew et al., "A New Percutaneous Vena Cava Filter,"*AJR*, vol. 141, Sep. 1983, pp. 601-604.

Cragg, Andrew et al., "Nonsurgical Placement of Arterial Endoprosthesis: A New Technique Using Nitinol Wire," *Radiology*, vol. 147, Apr. 1983, pp. 261-263.

Diethrich et al., "Percutaneous Techniques for Endoluminal Carotid Interventions," *J. Endovasc. Surg.*, vol. 3 (1996) pp. 182-202.

Fadali, A. Moneim, "A Filtering Device for the Prevention of Particulate Embolization During the Course of Cardiac Surgery," *Surgery*, vol. 64, No. 3, Sep. 1968, pp. 634-639.

Haïssaguerre et al., "Spontaneous Initiation of Atrial Fibrillation by Ectopic Beats Originating in the Pulmonary Veins," *The New England Journal of Medicine*, vol. 339, No. 10, Sep. 3, 1988, pp. 659-666.

Jordan, Jr. et al., "Microemboli Detected by Transcranial Doppler Monitoring in Patients During Carotid Angioplasty versus Carotid Endarterectomy," *Cardiovascular Surgery*, vol. 7, No. 1, Jan. 1999, pp. 33-38.

Karalis et al., "Recognition and Embolic Potential of Intraaortic Atherosclerotic Debris," *JACC*, vol. 17, No., Jan. 1991, pp. 73-78.

Knecht, Gregory L., M.D. et al., "Double-Channel Fistulotome for Endoscopic Drainage of Pancreatic Pseudocyst", *Gastrointestinal Endoscopy*, vol. 37, No. 3, May/Jun. 1991, pp. 356-357.

Lesh, "Can Cathether Ablation Cure Atrial Fibrillation?" *ACC Current Journal Review*, (Sep./Oct. 1997) pp. 38-40.

Lund et al., "Long-Term Patency of Ductus Arteriosus After Balloon Dilatation: an Experimental Study," *Circulation*, vol. 69, No. 4, Apr. 1984, pp. 772-774.

Marache et al., "Percutaneous Transluminal Venous Angioplasty in Occlusive Iliac Vein Thrombosis," *American Heart Journal*, vol. 125, No. 2, Pt 1, Feb. 1993, pp. 362-366.

Mazur et al., "Directional Atherectomy with the Omnicath™: A Unique New Catheter System," *Catheterization and Cardiovascular Diagnosis*, vol. 31, No. 1 (1994) pp. 17-84.

Moussa, MD, Issaam "Stents Don't Require Systemic Anticoagulation . . . But the Technique (and Results) Must be Optimal," *Journal of Invasive Cardiol.*, vol. 8, Supplement E, (1996) pp. 3E-7E.

Nakanishi et al., "Catheter Intervention to Venous System Using Expandable Metallic Stents," *Rinsho Kyobu Geka*, vol. 14, No. 2, (Apr. 1994) English Abstract Only.

Önal et al., "Primary Stenting for Complex Atherosclerotic Plaques in Aortic and Iliac Stenoses," *Cardiovascular & Interventional Radiology*, vol. 21, No. 5, Sep./Oct. 1998, pp. 386-392.

Siegel, Jerome H., M.D. et al., "Two New Methods For Selective Bile Duct Cannulation and Sphincterotomy", *Gastrointestinal Endoscopy*, vol. 33, No. 6, Dec. 1987, pp. 438-440.

Theron et al., "New Triple Coaxial Catheter System for Carotid Angioplasty with Cerebral Protection," *AJNR*, vol. 11, Sep./Oct. 1990, pp. 869-874.

Tunick et al., "Protruding Atheromas in the Thoracic Aortic and Systemic Embolization," *Annals of Internal Medicine*, vol. 115, No. 6, Sep. 15, 1991, pp. 423-427.

Tunick et al., "Protruding Atherosclerotic Plaque in the Aortic Arch of Patients with Systemic Embolization: A New Finding Seen by Transesophageal Echocardiography," *American Heart Journal*, vol. 120, No. 3, Sep. 1990, pp. 658-660.

Waksmann et al., "Distal Embolization is Common After Directional Atherectomy in Coronary Arteries and Saphenous Vein Grafts," *American Heart Journal*, vol. 129, No. 3, Mar. 1995, pp. 430-435.

Wholey, Mark H. et al., PTA and Stents in the Treatment of Extracranial Circulation, *The Journal of Invasive Cardiology*, vol. 8, Supplement E (1996) pp. 25E-30E.

U.S. Appl. No. 11/040,505, filed Jan. 21, 2005 to Chandra et al.

\* cited by examiner

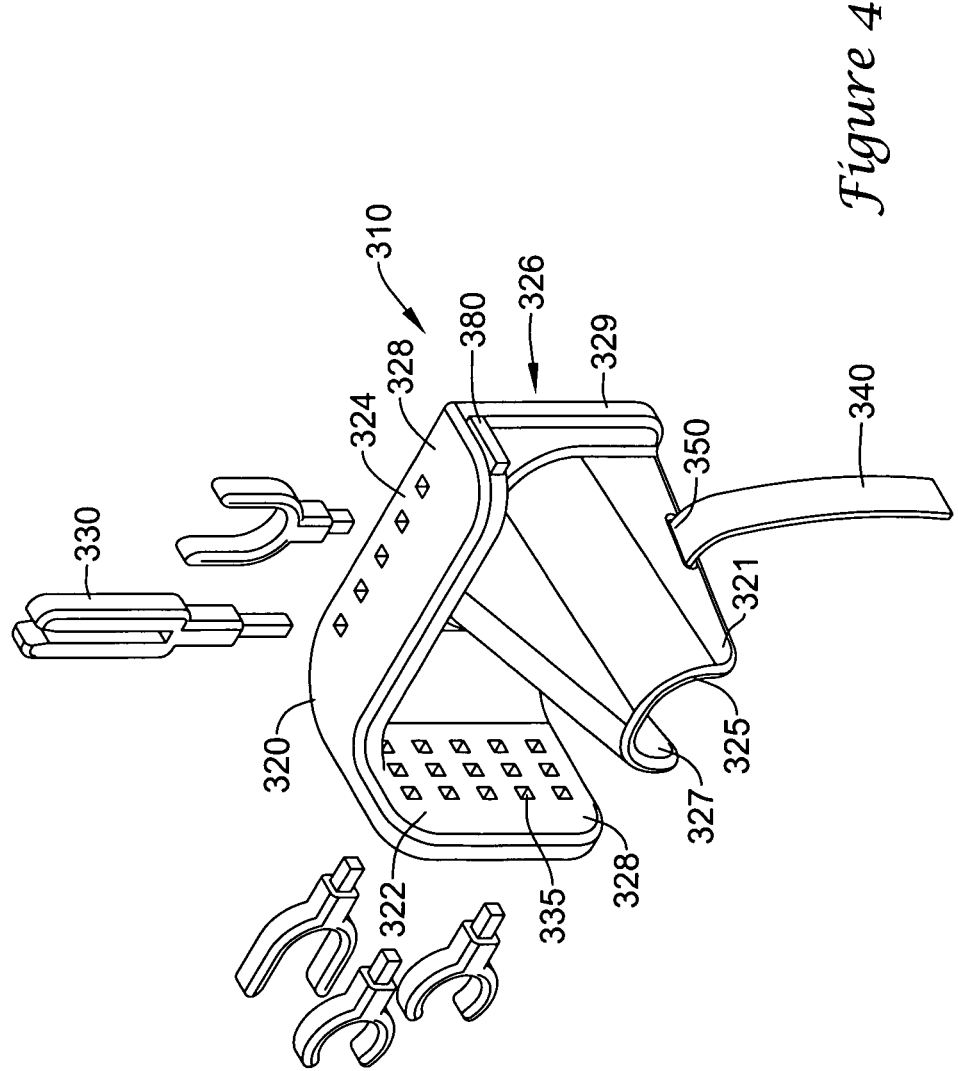

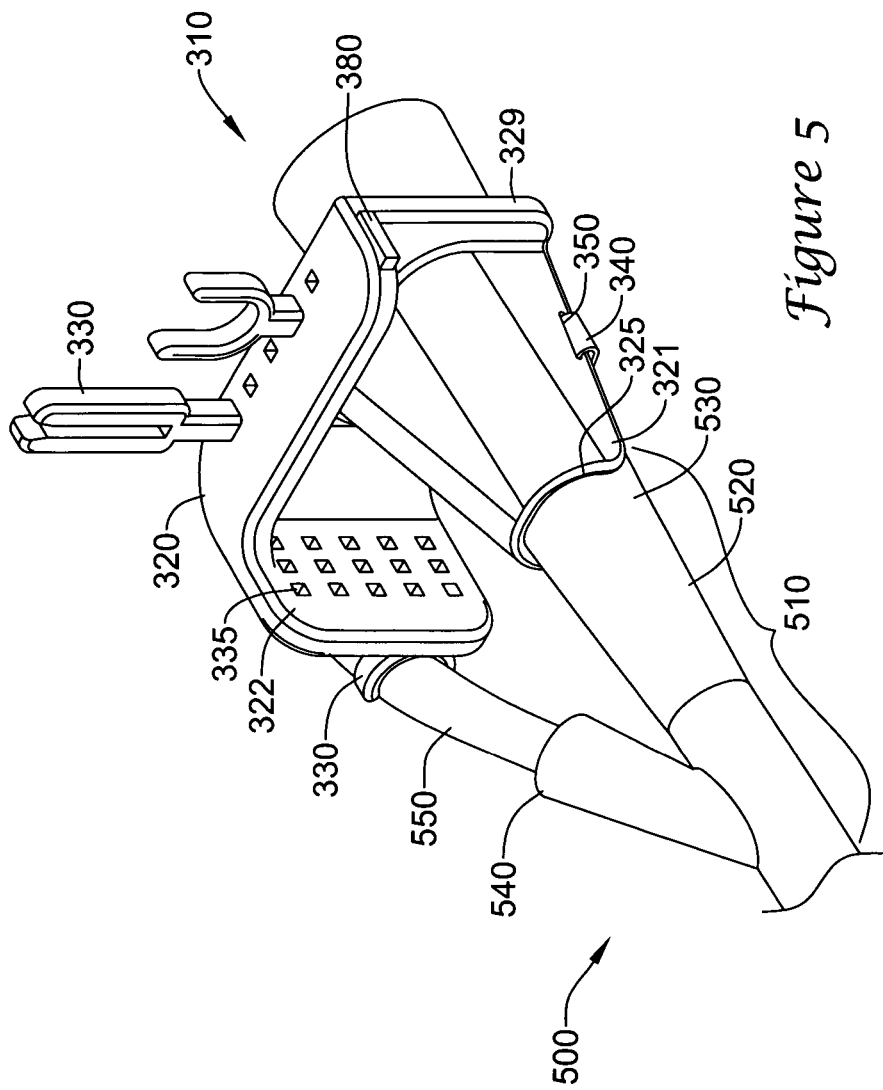

UNIVERSAL UTILITY BOARD FOR USE WITH MEDICAL DEVICES AND METHODS OF USE

FIELD OF THE INVENTION

The invention generally relates to fixtures for holding medical devices. More particularly, the invention relates to a fixture attached to an elongate medical device for holding a variety of medical instruments and methods for its use.

BACKGROUND OF THE INVENTION

Relatively non-invasive medical procedures are routinely performed on patients throughout the United States and the world. Many such procedures utilize a device including an elongate shaft. The elongate shaft may be inserted into a body cavity in order to navigate to a remote location within the body. Often the medical device is inserted into a natural body orifice, such as the nose, mouth, anus, bladder or vagina. In some procedures, a small surgical incision may be created at a convenient location in the skin of the patient where the elongate shaft of the device may be inserted into the body. Once the medical device is inserted into a body, an operator may then maneuver the medical device within the body to a remote location.

Once positioned in a body, additional medical devices may be advanced through the elongate shaft in order to reach a remote location in the body for performing a medical procedure. Often, it is necessary or useful to control and operate such medical devices simultaneously and/or consecutively during a procedure.

For example, an endoscopic procedure, such as gastroscopy, sigmoidoscopy and colonoscopy, may be performed with a flexible elongate shaft called an endoscope. The endoscope may be passed through a body cavity to a target location. Once at the target location, additional medical devices such as catheters, snares, forceps, cytology brushes, cautery probes, and the like, may be passed through the endoscope. Often, multiple devices may be operated within the endoscope during a single medical procedure.

There is an ongoing need to provide a way for an operator to simultaneously and/or consecutively control and operate multiple devices during a medical procedure.

SUMMARY OF THE INVENTION

The invention is generally directed to a fixture coupled to a medical device. The fixture may be configured to hold medical instruments during a medical procedure, freeing the operator's hand from holding the medical instrument. Therefore, the fixture may provide an operator with the ability to control multiple instruments during a medical procedure. Additionally, the fixture may alleviate the need for additional assistance, such as from a nurse or technician, during a medical procedure.

Accordingly, one representative embodiment of the invention is a fixture or utility board which may be attached to a proximal portion of a medical device, such as the handle of an endoscope. The utility board may include at least one, and preferably a plurality of grasping devices or receptacles for receiving and retaining medical devices used during a medical procedure, such as an endoscopic procedure.

BRIEF DESCRIPTION OF THE DRAWINGS

The invention may be more completely understood in consideration of the following detailed description of various embodiments of the invention in connection with the accompanying drawings, in which:

FIG. 4 is a perspective view of another representative utility fixture in accordance with the invention; and FIG. 5 is a perspective view of a representative utility fixture secured to an elongate medical device in accordance with the invention.

DETAILED DESCRIPTION OF PREFERRED EMBODIMENTS

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention.

Figure 1:
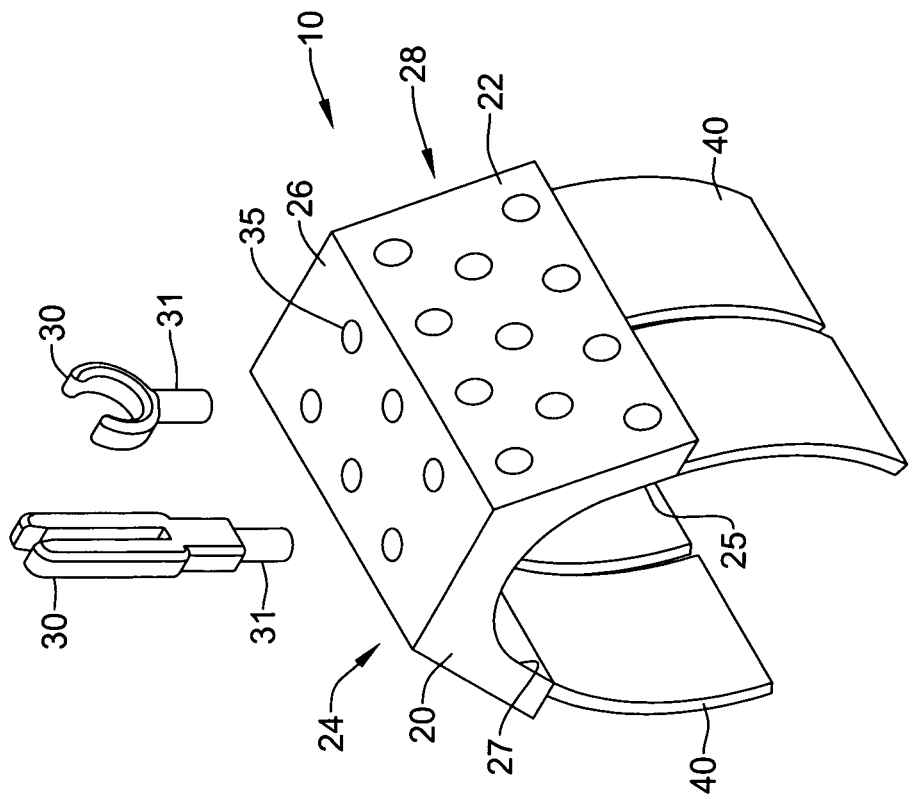
FIG. 1 is a perspective view of a representative utility fixture in accordance with the invention.

FIG. 1 illustrates one exemplary embodiment of the invention. Fixture 10 may include a body 20. Body 20 may be a multi-piece construction, a two-piece construction, or a one-piece construction. Body 20 may include metals, metal alloys, polymers, polymer blends, and the like. Some examples of materials for use in body 20 may include stainless steel, titanium, polyethylene (PE), high density polyethylene (HDPE), low density polyethylene (LDPE), polycarbonate (PC), polyamide (PA), polyimide (PI), polypropylene (PP), polystyrene (PS), polyvinyl chloride (PVC), liquid crystal polymer (LCP), or alloys, mixtures, combinations, copolymers thereof, polymer/metal composites, and the like. Alternative materials may be used for portions of the body 20, and the invention is not intended to be limited by the materials used for the body 20.

Body 20 may include a plurality of surfaces, such as first side 22, second side 24, top 26, and end 28. Surfaces 22, 24, 26, 28, or any subset thereof, may include means for retaining receptacles 30 such as holes, recesses, slots, channels, clips, pegs, magnets, fasteners, springs, adhesive, and the like. Additional means for retaining receptacles may include spring operated mechanisms, a lock and key mechanism wherein the receptacle 30 may be inserted into a key hole and rotated into a secured position, a malleable foam encompassing at least a portion of a receptacle 30, a compliant polymer providing an interference fit, and the like. As shown in FIG. 1, a plurality of recesses 35 may be formed in one or more surfaces 22, 24, 26, 28 of body 20. Recesses 35 may extend through body 20 or recesses may terminate at a location within body 20. A plurality of recesses 35 may be disposed uniformly on a surface such as to form a grid pattern. Recesses 35 may be designed to securely receive shaft 31 of receptacle 30. Recesses 35 may be of any shape and size. For instance, recesses 35 may be round or square. Recesses 35 may include a means for retaining receptacle 30. For example, recesses 35 may be threaded, tapered, grooved, or may provide other means for retaining receptacle 30, such as providing an interference fit, a mechanical locking mechanism, a spring locking mechanism, a foam or compliant polymer, a key and keyhole securing mechanism, adhesive, and the like.

Body 20 may include a recessed portion 25 which may be formed to fit a proximal portion of an elongate medical device, such as the handle of an endoscope. Recessed portion 25 may include a concave surface 27 formed in body 20 as shown in FIG. 1. Recessed portion 25 having a concave surface 27 may conform around a proximal portion of an elongate device such as a handle of an endoscope. Recessed portion 25 of body 20 may allow fixture 10 to be positioned about a portion of an outer surface of a proximal portion of a medical device. Recessed portion 25 may extend substantially the entire length of body 20, such that fixture 10 may be positioned at a location distal the proximal end of the medical device.

Fixture 10 may include a means, such as straps 40, for securing body 20 to a proximal portion of an elongate medical device. Such means may include an adjustable strap, an elastic strap, an inelastic strap, a Velcro-type hook and loop strap, snaps, ties, clips, pins, adhesive, fasteners, and the like. Additional securing means such as a snap-fit, wedge-fit, magnetism, and the like, may also be employed in the invention to secure body 20 to an elongate medical device. It is also contemplated that body 20 may be integrally formed in a proximal portion of an elongate medical device.

Fixture 10 may also include one or more receptacles 30 designed to retain additional medical devices and accessories. Receptacles 30 may be hooks, clamps, clips, pivot members, pegs, straps, fasteners, magnets, springs, spring operated mechanisms, and the like. Receptacles 30 may include a plurality of fingers or grasping members for grasping a medical device. Receptacles 30 may include materials such as those listed above regarding body 20. Receptacles 30 may include a foam, a compliant polymer, or the like, or receptacle 30 may include a malleable insert comprising a foam, compliant polymer, fibrous material, or the like. Such materials may be configured to selectively yield when exposed to an applied force. Therefore, such materials may retain a medical device by yielding when a medical device is placed adjacent the material and force applied. The material may be urged to surround a portion of a medical device, thereby retaining the device. Alternative materials may be used for portions of the receptacles 30, and the invention is not intended to be limited by the materials used for the receptacles 30. Receptacles 30 may be designed to accommodate a specific medical device, or receptacles 30 may be generally designed to accommodate medical devices. For example, receptacle 30 may include grasping members of different sizes and spacing to accommodate various shapes and sizes of medical devices. A combination of receptacles 30 may be chosen to accommodate medical devices used during a specific medical procedure. Receptacles 30 may include a means for retaining receptacles 30 to body 20, such as means complementary to those provided in surfaces 22, 24, 26, 28. For example, shaft 31 of receptacles 30 may include a male threaded portion and recesses 35 may include a female threaded portion, or receptacles 30 may include an interference fit member adapted to generate an interference fit with recesses 35.

Figure 2A:
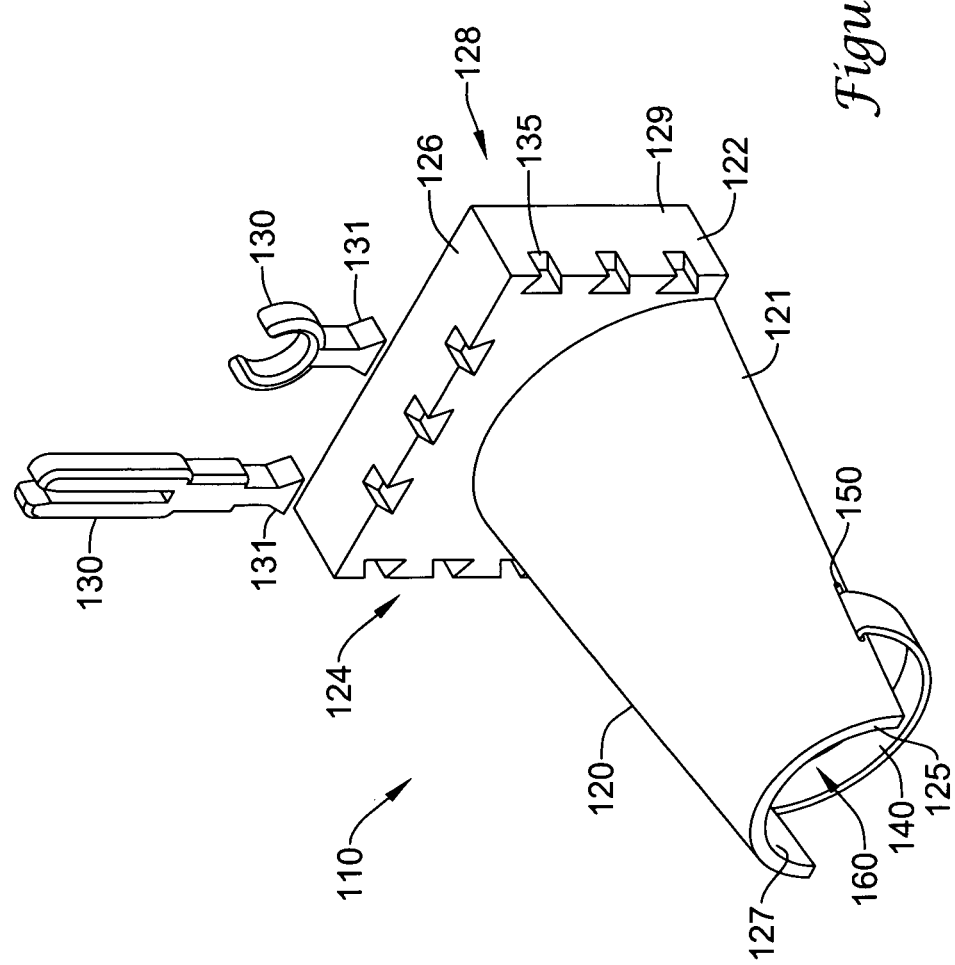
FIGS. 2A-2B are perspective views of another representative utility fixture in accordance with the invention.
Figure 2B:
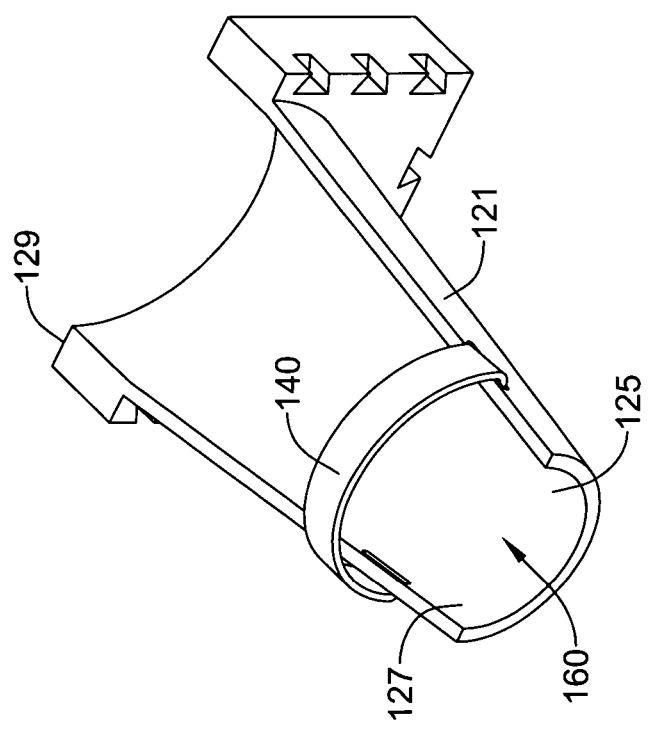

FIGS. 2A-2B illustrate another fixture 110 similar to fixture 10. Fixture 110 includes a body 120 having a truncated conical shell portion 121 and a block portion 129. Body 120 may include a recessed portion 125 having a concave surface 127 defined in the truncated conical shell portion 121 and/or the block portion 129. The truncated conical shell portion 121 including a recessed portion 125 having a concave surface 127 may more easily be understood from FIG. 2B, which shows the underside of fixture 110. Recessed portion 125 may be defined as a cavity formed in fixture 110. Recessed portion 125 may be formed to accommodate a proximal portion of an elongate medical device. For example, truncated conical shell portion 121 having a concave surface 127 may accommodate a tapered handle portion of an elongate device. Therefore, fixture 110 may fit securely about a portion of an elongate medical device, such that the concave surface 127 abuts and conforms to the outer surface of an elongate medical device.

Body 120 may include an opening or eyelet 150. Eyelet 150 may be located along a portion of body 120 to provide a means for securing fixture 110 to an elongate medical device. Body 120 may include a plurality of eyelets 150. For example fixture 110 may include two eyelets 150. However, fixture 110 may include one, two, three, four, five, six, or more eyelets 150. For example, a pair of eyelets 150 may be disposed on either side of truncated conical shell portion 121, such that a fastening strap may extend between eyelets 150 as shown in FIG. 2A. Eyelet 150 may include an elongated slot formed in body 120, or eyelet 150 may be a separate component secured to body 120.

A fastener 140 may be provided to secure body 120 to a proximal portion of an elongate medical device. Fastener 140 may be an inelastic strap, an elastic strap, a Velcro-like strap having hooks and loops, or a releasable locking strap, for example. Fastener 140 may pass through eyelet 150, such that the strap extends from one eyelet 150 to an opposing eyelet 150. Such an arrangement allows an elongate medical device to pass through opening 160 defined between fastener 140 and concave surface 127 of recessed portion 125. Fastener 140 may be elastically contracted to secure fixture 110 to an elongate medical device. Alternatively or additionally, fastener 140 may be made taut such that fixture 110 is secured to an elongate medical device. Fixture 110 may be secured to an outer surface of a proximal portion of an elongate medical device.

Block portion 129 may include one or more surfaces, such as first side 122, second side 124, top 126 and front 128. Block portion 129 may include a means for receiving receptacle 130, such as one or more retaining channels 135. Retaining channel 135 may be located on one or more surfaces 122, 124, 126, 128 of block portion 129. Retaining channel 135 may be configured to receive one or more receptacles 130. As shown in FIG. 2A, retaining channel 135 may resemble a mortise and receptacle 130 may include a protrusion portion 131 resembling a tenon, such that receptacle 130 may be coupled in channel 135 to form an interlocking joint, such as a dovetail-type joint, or the like. Additional complementary geometries and/or connectors may be used to connect receptacles 130 to fixture 110 without departing from the scope of the invention.

Fixture 110 may include one or more receptacles 130. Receptacle 130 may be configured to receive and restrain an elongate medical device. For example, receptacle 130 may include a clip, hook, slot, clamp, clip, pivot member, peg, strap, fastener, magnet, spring, spring operated mechanism, and the like for receiving a portion of an elongate medical device. Receptacle 130 may include grasping members or fingers for grasping a medical device. Receptacles 130 may include a foam, a compliant polymer, or the like. Receptacle 130 may include a connection means, such as a protrusion portion 131, which may resemble a tenon. Protrusion portion 131 may have a square, rectangular, or circular base, for example, and protrusion portion 131 may have a tapered profile. Protrusion portion 131 of receptacle 130 may be sized to complement a retaining channel 135 in block portion 129. Such a configuration may provide an interlocking joint, such as a dovetail-type engagement between receptacle 130 and channel 135.

Figure 3:
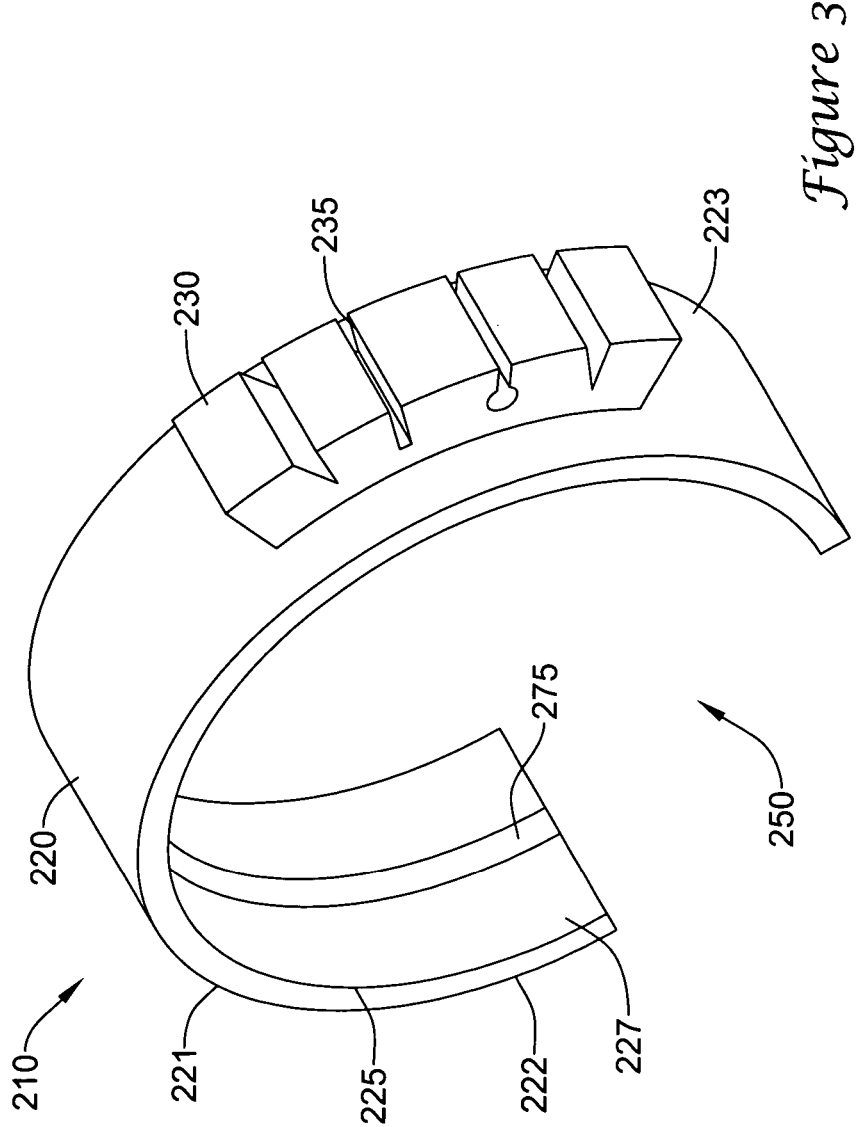
FIG. 3 is a perspective view of another representative utility fixture in accordance with the invention.

FIG. 3 illustrates another fixture 210 similar to fixture 10. Fixture 210 includes a body 220 connected to a receptacle 230. Receptacle 230 may be integrally formed in a portion of body 220 during a molding process well-known in the art. Alternatively, receptacle 230 may be separately formed and adhesively or thermally bonded to body 220, or receptacle 230 may be coupled to body 220 by additional securing means, such as with one or more fasteners and the like. Body 220 may comprise a cylindrical shell or a truncated conical shell, for example. Body 220 may include a recessed portion 225 defined by the inner surface 227 of fixture 210. Recessed portion 225 may be sized to accommodate a proximal portion of an elongate device, such that inner surface 227 of body 220 may be disposed about the outer surface of a proximal portion of an elongate medical device. Body 220 may include a slot or opening 250 creating a discontinuity in the wall of shell 221, such that body 220 may include a first wing 222 and a second wing 223. Body 220 may be placed over a proximal portion of a medical device, such that first wing portion 222 and second wing portion 223 are compelled to expand outward. Wing portions 222, 223 may be configured such that they attempt to return to their static state once placed about a portion of a medical device, therefore placing a resultant compressive force about a portion of an elongate device encircled by body 220 of fixture 210. Such resultant compressive force may securely maintain fixture 210 about a proximal portion of an elongate medical device due to retention and frictional forces created between body 220 and an elongate medical device. Thus, the securement of fixture 210 to a medical device may be characterized as a snap fit or interference fit.

Alternatively or additionally, body 220 may include one or more protrusions or ribs 275 formed on a portion of inner surface 227. Rib 275 may be sized to accommodate a complementary geometry, such as a slot or groove, formed in a portion of a medical device. Rib 275 may position fixture 210 and restrain fixture 210 from moving on a medical device once coupled to the device. It is noted that fixture 210 may include one or more slots or grooves, and a medical device may include one or more corresponding protrusions or ribs without departing from the scope of the invention. Complementary geometry of fixture 210 and a medical device may provide a snap-fit or interference fit to secure fixture 210 to a medical device.

Receptacle 230 may include means for retaining a medical device. For example, receptacle 230 may include one or more securing members, such as indentations 235, for receiving a portion of a medical device. Indentation 235 may be generally configured to receive a medical device, or indentation may be specifically configured to receive a particular medical device. For example, indentation 235 may be a slot, a tapered groove, a keyhole slot, a notch, and the like. Indentation 235 may be sized as to restrict longitudinal movement of an elongate device secured in indentation 235. Receptacle 230 may, alternatively or additionally, include one or more clips, clamps, magnets, hooks, serrations, fasteners, springs, spring operated mechanisms, foam, compliant polymer, and the like, capable of receiving and retaining a medical device.

FIG. 4 illustrates another fixture 310 similar to fixture 10. Fixture 310 may include a body 320 having a recessed region such as a truncated conical shell portion 321 and a block portion, such as a face plate 329, attached to truncated conical shell portion 321. Truncated conical shell portion 321 may be integrally formed with face plate 329 to form body 320 or truncated conical shell portion 321 may be attached to face plate 329, such as by an adhesive, thermal bond, fasteners, and the like, as to define body 320. Truncated conical shell portion 321 may include a concave surface 327 sized to encompass at least a portion of an elongate device. Concave surface 327 of truncated conical shell portion 321 may define a cavity or recessed portion for receiving a portion of an elongate medical device. It is noted that truncated conical shell portion 321 alternatively may be a cylindrical shell portion or other recessed region shaped for receiving a portion of a medical device.

Face plate 329 may include one or more surfaces or faces 328. As shown in FIG. 4, fixture 310 may include at least one, and preferably a plurality of faces 328. A first face 322 may be positioned in a first plane, a second face 324 may be positioned in a second plane, and a third face 326 may be positioned in a third plane. Although fixture 310 shown in FIG. 4 includes three faces, fixture 310 may include one, two, three, four, five, six, or more faces. The faces, such as faces 322, 324, 326, may be positioned such that they intersect one another, or faces 322, 324, 326 may be substantially parallel with one another. Faces 322, 324, 326 may be molded to form a single integral member, or faces 322, 324, 326 may be formed separately and attached to fixture 310 in a subsequent attachment process. Alternatively or additionally, fixture 310 may include at least one face 328 having a curved portion. A curved portion may enhance aesthetic and/or ergonomic concerns. For instance, a fixture 310 having a curved face may minimize movements made by an operator and/or position receptacle 330 for unobstructed access by an operator.

Face 328 may include one or more recesses or holes 335. Holes 335 may extend through face 328 or holes 335 may terminate at a location within face 328. Preferably face 328 may include a grid of holes 335 arranged in a regular pattern, such that face 328 may resemble a peg-board. For example, face 328, such as face 322, may include five rows of three holes 335 each. However, face 328 may include any other arrangement of columns and rows of holes 335 as desired. For instance, face may include one, two, three, four, five, six, or more rows of holes 335 and one, two, three, four, five, six, or more columns of holes 335. Holes 335 may be substantially the same size and/or shape, or holes 335 may vary in size and/or shape throughout the fixture 310. For example, holes 335 of face 322 may have a diameter larger than holes 335 of face 324 which may have a diameter larger than holes 335 of face 326. The size and/or shape of holes 335 may provide an indicator as to what medical device apparatus is/are intended to be associated with select holes 335. Additionally or alternatively, receptacles 330, holes 335, or face 328 may be color-coded, stamped or labeled to provide visual indication to an operator.

Fixture 310 may include one or more release switches 380. Release switch 380 may be a push button, a lever, a slide, or the like. Release switch 380 may include a lock position and an unlock position, wherein the lock position preferably is the default position. Release switch 380 may provide a means to releasably secure receptacles 330 to fixture 310. For example, release switch 380 may be a quick release switch having a spring actuated member moving from a first, lock position to a second, unlock position. Receptacles 330 may be selectively released from fixture 310 by switch 380. Receptacles 330 positioned in holes 335 may be secured to fixture 310 when switch 380 is in the lock position, and receptacles 330 may be removed from or repositioned in holes 335 when switch 380 is actuated to the unlock position.

Fixture 310 may include a means for securing fixture 310 to a proximal portion of an elongate medical device. For example, fixture 310 may include one or more openings or eyelets 350. As shown in FIG. 4, a pair of eyelets 350 may be located on either side of truncated conical shell portion 321. However, fixture 310 may include one, two, three, four, five, six, or more eyelets 350. Eyelet 350 may include an elongated slot formed in fixture 310 or eyelet 350 may be a separate component secured to fixture 310.

A fastener 340 similar to fastener 140 may be provided to secure fixture 310 to a proximal portion of an elongate medical device. Fastener 340 may be an inelastic strap, an elastic strap, a Velcro-like strap having hooks and loops, or a releasable locking strap, for example. Fastener 340 may pass through eyelet 350, such that strap extends from one eyelet 350 to an opposing eyelet 350. Alternatively or additionally, fastener 340 may be attached to fixture 310 and extend through eyelet 350 to secure fixture 310. Such an arrangement may allow fixture 310 to be positioned on a proximal portion of an elongate medical device. An elongate medical device may be disposed between the inner surface 327 of truncated conical shell portion 321 and fastener 340. Fastener 340 may be elastically contracted to secure fixture 310 to an elongate medical device. Alternatively or additionally, fastener 340 may be made taut such that fixture 310 is secured to an elongate medical device. Therefore, fixture 310 may be disposed about an outer surface of an elongate medical device and secured thereto.

Other means may be used to secure fixture 310 to a medical device. For instance, fixture 310 may be secured to a medical device by adhesive, snap fit, magnetism, fasteners, mechanical interlocking, spring operated mechanisms, and the like. Fixture 310 may be temporarily secured to a medical device or fixture 310 may be permanently secured to a medical device.

Fixture 310 may include one or more receptacles 330 for receiving and retaining one or more additional medical instruments. Receptacle 330 may be a clip, clamp, hook, notch, groove, slide, magnet, strap, peg, pin, tie, spring, spring operated mechanism, foam, compliant polymer, and the like. Receptacle 330 may be configured to receive a specific medical instrument, or receptacle 330 may be configured to receive medical instruments generally. A combination of several receptacles 330 may be used during a medical procedure. Receptacle 330 may include gripping members or fingers including a gripping surface having serrated edges for grasping a medical device, receptacle 330 may include a foam or compliant polymer, or receptacle 330 may include a substantially smooth surface.

FIG. 5 illustrates fixture 310 secured to an elongate medical device 500. Elongate medical device 500 may have a proximal portion 510 including a handle 520. Handle 520 may extend substantially through recessed portion 325 of fixture 310. Elongate medical device 500 may have at least one access port 540 for accessing a lumen (not shown) of elongate medical device 500. Access port 540 may receive a medical instrument 550, wherein a distal portion of medical instrument 550 may extend into the lumen of elongate medical device 500 and a proximal portion may extend out of access port 540 external of elongate medical device 500. Fixture 310 may be disposed about a portion of elongate medical device 500 such that recessed portion 325 of fixture 310 conforms to an outer surface 530 of elongate medical device 500. Fastener 340 may extend around elongate medical device 500 to secure fixture 310, such that elongate medical device 500 is at least partially surrounded by recessed portion 325 and fastener 340. Fixture 310 may be secured to outer surface 530 of elongate medical device 500 at a location proximal of access port 540. Receptacle 330 may receive a proximal portion of medical instrument 550 extending out of access port 540 and external of elongate medical device 500.

A utility board, such as fixture 310, may be used in a variety of procedures. An elongate device may be advanced to a target location in a body. A utility board, such as fixture 310, may be secured to the elongate device prior to or subsequent the advancement of the elongate device to a target location. Fixture 310 may be secured to an outer surface of a proximal portion of an elongate medical device. A receptacle, or preferably a combination of receptacles 330, may be coupled to the body 320 of fixture 310. The combination of receptacles 330 may be chosen depending on what medical procedure will be performed and/or what medical instruments will be used during a procedure. Receptacle 330 may be coupled to the body 320, such as by inserting receptacle 330 in hole 335 at a convenient location. Receptacle 330 may be retained in hole 335 by securing means, such as those discussed above. Additional receptacles 330 may be inserted in holes 335 as desired. One or more additional medical instruments may be advanced through the elongate medical device. The one or more additional medical instruments may exit the elongate medical device at a location distal the fixture 310, or the one or more medical instruments may extend substantially to the proximal end of the elongate medical device. For example, a medical instrument may exit the elongate medical device at an access port distal the proximal end of the elongate medical device. Alternatively a medical instrument may exit the elongate medical device at a proximal end of the medical device. Receptacle 330 may receive and retain a medical instrument, such that the operator need not continuously hold the instrument, thus the operator is able to free a hand to perform additional tasks during a procedure. Therefore, the operator may simultaneously or consecutively control multiple instruments during a medical procedure. With the instrument retained in a receptacle 330, the operator may actuate the instrument or control another medical device without additional assistance.

An exemplary procedure may utilize a fixture 310 secured to a proximal portion of an elongate device, such as the handle of an endoscope. An endoscope may be inserted into a body and advanced to a target location, such as a location within the body for taking a biopsy. The operator may then pass an elongate device, such as a biopsy forceps through the access port of the endoscope to the target location. An exposed portion of the elongate device, such as the biopsy forceps handle, may be retained in a receptacle 330 of fixture 310. Thereafter, the operator may maneuver the endoscope and operate the handle of the biopsy forceps without assistance. Therefore, fixture 310 may be deemed to provide an operator with a third or free hand during a medical procedure such that additional assistance from a nurse or technician may be unnecessary.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A utility fixture for use with a medical device comprising:
   a utility board comprising:
      a recessed member having a first side including a convex surface, a second side that faces a direction opposite the first side and includes a concave surface, and a first length extending from a proximal end of the convex surface to a distal end of the convex surface; and
      a block having a second length extending from a proximal end of the block to a distal end of the block, and disposed, at least in part, on the convex surface of the recessed member, wherein the concave surface of the recessed member is sized to receive a proximal portion of the medical device along the concave surface, wherein the block includes a grid of holes for receiving the one or more receptacles; and
   one or more receptacles for receiving a medical instrument, wherein one or more receptacles are disposed on the block during use,
   wherein the first length is equal to or greater than the second length; and
   wherein an orientation of the recessed member is fixed relative to an orientation of the block throughout operation of the utility fixture.

2. The fixture of claim 1, wherein the concave surface is configured to abut an outer surface of the medical device.

3. The fixture of claim 1, wherein the recessed member includes a truncated conical shell comprising the concave surface and the convex surface.

4. The fixture of claim 1, wherein the block includes one or more faces, wherein the one or more holes are disposed on the one or more faces.

5. The fixture of claim 1, wherein the one or more holes are threaded and the one or more receptacles include a complementary threaded portion.

6. The fixture of claim 1, wherein the one or more receptacles forms an interference fit with the block.

7. The fixture of claim 1, wherein the block includes two or more holes for receiving two or more receptacles simultaneously.

8. The fixture of claim 1, further comprising a fastener configured to fasten the utility board to the proximal portion of the medical device.

9. The fixture of claim 1, wherein the first length is greater than the second length.

10. The fixture of claim 1, wherein the block comprises a second concave surface, and
    wherein the second concave surface engages with the convex surface of the recessed member.

11. The fixture of claim 1, wherein the medical device received along the concave surface is different from the medical instrument received by the one or more receptacles.

12. The fixture of claim 1, wherein the convex surface has a width extending in a lateral direction from a first end of the recessed member to a second end of the recessed member,
    wherein the width is transverse to the first length, and
    wherein a surface of the block disposed on the convex surface extends continuously along the width of the convex surface.

13. The fixture of claim 1, wherein the recessed member extends distally from the block.

14. An apparatus for use during a medical procedure comprising:
    an elongate medical device having a proximal portion and an outer surface;
    a utility board having a length extending from a proximal end of the utility board to a distal end of the utility board, the utility board including a concave surface extending the length of the utility board, the concave surface disposed about and sized to conform to the proximal portion of the elongate medical device and detachable from the elongate medical device, wherein the utility board includes a grid of holes for receiving the one or more receptacles; and
    one or more receptacles for receiving a medical instrument, wherein the utility board includes a means for receiving the one or more receptacles on a convex surface of the utility board facing away from the concave surface of the utility board and within the length of the utility board,
    wherein the one or more receptacles extend away from the convex surface when the proximal portion of the medical device is secured to the concave surface.

15. The apparatus of claim 14, wherein the one or more receptacles are detachable from the utility board.

16. The apparatus of claim 14, wherein the grid of holes is disposed on a body having one or more faces.

17. The apparatus of claim 14, wherein the utility board includes one or more channels for receiving the one or more receptacles and the one or more receptacles includes a protrusion sized to interlock with the one or more channels.

18. The apparatus of claim 14, wherein the utility board includes a switch for selectively releasing the one or more receptacles from the utility board.

19. The apparatus of claim 14, wherein the utility board includes a recessed portion having the concave surface and conforming to the outer surface of the elongate medical device.

20. The apparatus of claim 14, wherein the proximal portion of the elongate medical device, includes a handle, wherein the utility board is disposed about a portion of the handle.

21. The apparatus of claim 14, wherein the utility board includes a means for receiving two or more receptacles simultaneously on the second surface.

22. The apparatus of claim 14, further comprising a fastener configured to fasten the utility board to the proximal portion of the elongate medical device.

23. The apparatus of claim 14, wherein the elongate medical device received along the concave surface is different from the medical instrument received by the one or more receptacles.

24. A method of performing a medical procedure using an elongate medical device having a proximal portion and an outer surface, and a utility board having a convex side including one or more receptacles for retaining medical instruments, the method comprising the steps of:
    securing a concave side facing a direction opposite of the convex side of the utility board to the proximal portion of the elongate medical device such that the proximal portion of the elongate medical device extends substantially along the concave side;
    advancing the elongate medical device to a target location in a body;
    advancing a medical instrument through the elongate medical device to the target location; and
    retaining the medical instrument in the one or more receptacles of the utility board;
    wherein the convex side has a first length extending from a proximal end of the convex side to a distal end of the convex side;

wherein the concave side has a second length extending from a proximal end of the concave side to a distal end of the concave side; and wherein the second length is longer than the first length.

25. The method of claim 24, further comprising the step of: actuating the medical instrument retained in the one or more receptacles.

26. The method of claim 24, further comprising the step of: maneuvering the elongate medical device and medical instrument simultaneously.

27. The method of claim 24, further comprising the step of: controlling another medical device while retaining the medical instrument in the one or more receptacles of the utility board.

28. The method of claim 24, wherein the one or more receptacles are detachable from the utility board.

29. The method of claim 24, wherein the concave side conforms to the outer surface of the elongate medical device.

30. The method of claim 24, wherein the medical instrument is exposed exterior of the elongate medical device at a location distal of the utility board.

31. The method of claim 24, wherein the elongate medical device has an access port disposed distal of the utility board, wherein the medical instrument is advanced through the access port.

32. The method of claim 24, wherein the proximal portion of the elongate medical device includes a handle, wherein the utility board is secured to a portion of the handle.

33. The method of claim 24, wherein the convex side of the utility board includes two or more receptacles for retaining two or more medical instruments simultaneously.

34. The method of claim 24, wherein the elongate medical device secured to the concave side is different from the medical instrument retained in the one or more receptacles.

* * * * *